United States Patent [19]

Vahlensieck et al.

[11] 4,028,384
[45] June 7, 1977

[54] PROCESS FOR THE PREPARATION OF ORGANIC SILICON COMPOUNDS

[75] Inventors: Hans-Joachim Vahlensieck, Wehr; Claus-Dieter Seiler; Hans-Joachim Kötzsch, both of Rheinfelden, all of Germany

[73] Assignee: Dynamit Nobel Aktiengesellschaft, Troisdorf, Germany

[22] Filed: Nov. 23, 1973

[21] Appl. No.: 418,793

Related U.S. Application Data

[63] Continuation of Ser. No. 58,189, July 24, 1970, abandoned.

[30] Foreign Application Priority Data

July 25, 1969  Germany ........................... 1937904

[52] U.S. Cl. .......................... 260/347.8; 260/340.9; 260/348 SC; 260/448.2 E
[51] Int. Cl.² ................... C07D 307/12; C07F 7/02
[58] Field of Search ................. 260/448.2 E, 340.9, 260/347.8, 348 SC

[56] References Cited

UNITED STATES PATENTS

| | | | |
|---|---|---|---|
| 3,470,225 | 9/1969 | Knorre et al. ................. | 260/448.2 |
| 3,624,119 | 11/1971 | Rothe et al. ................... | 252/429 R |

*Primary Examiner*—Henry R. Jiles
*Assistant Examiner*—Bernard Dentz
*Attorney, Agent, or Firm*—Burgess, Dinklage & Sprung

[57] ABSTRACT

The use of certain chloroplatinic complex compounds of the formula:

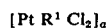

$$[Pt\ R^1\ Cl_2]_a$$

wherein $a$ is 1 or 2 and $R^1$ is an unsaturated ketone residue, to catalyze the addition of alkoxy, aryloxy or halo hydrogen silanes to aliphatically unsaturated compounds (carbon to carbon unsaturation such as olefins and/or acetylenes). The products of the reaction can be used as additives for plastics and synthetic resins.

20 Claims, No Drawings

PROCESS FOR THE PREPARATION OF ORGANIC SILICON COMPOUNDS

This is a continuation of application Ser. No. 58,189 filed July 24, 1970 now abandoned.

This invention relates to the preparation of organic silicon-containing compounds. It more particularly refers to a novel catalyst for use in the preparation of such compounds.

In the prior art, hexachloroplatinic acid hexahydrate has been described as a catalyst for the addition reaction of hydrogen silanes and alkenyl compounds. It has been found, however, that frequently, even under intensified reaction conditions, these reactions come to a premature stop or slow down progressively because of catalyst poisoning. Furthermore, undesired secondary or side reactions take place, such as the disproportionation of the hydrogen silanes used as starting materials, or the polymerization of reactants and/or addition products thereof. These side reactions cause considerable disturbance to the course of the main reaction and cause the desired main reaction yield to be diminished.

Many attempts have therefore been made to improve the performance of these reactions. In particular, it has been attempted to use other platinum compounds as catalysts rather than the hexachloroplatinic acid. For example, alcoholates and enolates of platinum, and platinum complexes with organic compounds containing olefin, aldehyde, amine and/or phosphine groups have been described for this use. Usually these newer catalysts are platinum compounds having two organic radicals therein, which can be described by the general formula $PtABy_2$, wherein $y$ is one or two halogens and A and B are identical or different organic ligands. It has been found, however, that these new types of platinum catalyst compounds offer few advantages over hexachloroplatinic acid hexahydrate, and that they have not been successful in fully eliminating the difficulties described above.

For this reason there has been a marked interest in the development of newer and different catalysts for the hydrosilyation reaction which do not induce secondary or side reactions of the types described above with reactive and sensitive functional groups, but which new catalysts at the same time are highly active with respect to the main, desired reaction so as to assure smooth operation of this reaction.

One of the aspects of this invention is based on the discovery that complex compounds of the general formula:

$$[Pt\,R^1\,Cl_2]_a$$

wherein $R^1$ is an unsaturated (olefinically unsaturated) ketone residue and wherein $a$ is one (1) or two (2), have excellent properties which enable such complex compounds to catalyze the hydrosilylation reaction of an aliphatically unsaturated compound and a hydrogen silane with a minimum of undesirable side effects and side reactions. It is particularly surprising that the catalytic activity of the complex compounds described herein is so high and so reliable, that is, they are active and directing catalysts, that it is possible to cause even large quantities of reagents to react completely and uniformly in no more than about 30 minutes. This attribute, in turn, permits the use of an especially advantageous method of carrying out the intended reaction. The catalyst concentrations useful according to the invention are between about $10^{-2}$ and $10^{-8}$ millimoles per mole of hydrogen silane reactant, preferably between about $10^{-3}$ and $10^{-6}$ millimoles per mole.

The catalysts of the invention are suitable for use in hydrosilylation both in batch operation and in continuous procedures.

It is preferable to work with equimolar amounts of hydrogen silane and unsaturated reactants, but if desired an excess of one or the other of the two reactants can be used. In the case of discontinuous or batch procedures, a small amount of the unsaturated reactant can be placed in a suitable reactor together with the catalyst and the mixture then heated to the reaction temperature. It should be noted that the reaction temperature may differ somewhat depending upon the particular olefin or acetylene compounds and/or upon the particular hydrogen silane component. Cold hydrogen silane reactant can then begin to be fed to the reaction system whereupon the reaction starts up immediately and continues, with moderate cooling and the feeding of additional cold unsaturate and hydrogen silane reactants until the reaction is complete. The reactants react very rapidly and in substantially quantitative yields.

Surprisingly, even with an increasing concentration of product in the reaction vessel there is scarcely any slowing of the reaction, so that by the time the feed has been shut off the hydrosilylation reaction has substantially ended. In the case of continuous operation, a mixture of the two reactants and the catalyst is heated to a suitable reaction temperature, depending again upon the exact nature of the reactants as noted above, in a pass-through heater in which the residence time is between about 1 and 20 minutes, preferably about 5 to 12 minutes, depending on the reagents and the catalyst, and the reaction is then allowed to continue for an additional 2 to 10 minutes. In this latter reaction period of 2 to 10 minutes substantially no additional heating is used. This post reaction period also causes a substantial homogenization of the reaction medium. It should be noted that this termination of heat input during this post reaction, homogenization period underscores the high activity of the catalysts of this invention. By way of comparison, hexachloroplatinic acid as well as platinum enolates containing halogen, for example, exhibit a substantially poorer catalytic activity, in that they require much longer reaction times. Such long reaction times favor secondary reactions and consequently result in lower yields.

The products prepared according to the invention are sufficiently pure for most applications, e.g., as additives for plastics and synthetic resins, sizes and finishes for use on glass, impregnating agents for metals, minerals, wood, textiles and paper, and as adhesives in the glass industry for a strong bond between glass and polymers, e.g., in glass fiber thermoplastics and glass staple fiber-reinforced polyvinylchloride, or in glass fiber, as in the case of polyester, polyepoxy or phenol-formaldehyde resins reinforced with glass fiber textiles.

The catalysts of the present invention, that is compounds of the general formula $[Pt\,R^1\,Cl_2]_a$ wherein $R^1$ and $a$ have the definitions set forth above, can be prepared in a simple manner by known methods of synthesis as set forth in Gmelin, 68 D, pp. 455–456. These catalysts compounds have excellent stability, are in crystalline form, have good shelf-life, and can be fed into the hydrosilylation reaction in the form of solutions thereof using, for example, ketones such as acetone, glycol ethers or the like or in some cases one of the two reactants as solvents, without adversely affecting their catalytic activity.

An especially preferred catalyst is the compound of the above general formula, in which $R^1$ is mesityl oxide. Other exemplary effective hydrosilylation catalysts within the meaning of the process of the invention, however, are those complexes wherein $R^1$ is butenone, phorone, isophorone, dihenzalacetone and other such unsaturated ketones.

Aliphatically unsaturated compounds which are capable of hydrosilylation by the process of this invention are carboncarbon unsaturated organic compounds, such as alkenes—examples being ethylene, propylene, 1,1,1-trifluoropropene-(2), butene-(1), butene-(2), isobutene, octene-(1), decene-(1), cyclohexene, styrene, cyclopentadiene, cyclododecatriene, etc.—and alkines such as acetylene, propine, butine-(2) etc. Of particular interest in this invention are unsaturated organic reactants containing additional functional substitutent groups, such as for example unsaturated ethers, such as divinyl ether, diallyl ether, ethylene glycol diallyl ether, diethylene glycol diallyl ether, the polyethylene and/or propylene glycol diallyl ethers, glycidyl allyl ethers, 2-allyl-oxymethyltetrahydrofuran, 2,2-dimethyl-4-allyloxymethyldioxolane, 4-allyloxymethyldioxolone-(2), 2-allyloxyheptafluoropropane, 2-allyloxy-1,1,1,3,3,3-hexafluoropropane, etc.; esters and thioesters of unsaturated alcohols, e.g., vinyl and allyl esters of organic acids such as acetic acid, propionic acid, thioacetic acid, 2-ethylcapronic acid, lauric acid, isophtahlic acid, terephthalic acid and the hydrogen halide acids such as hydrochloric, etc.; unsaturated organic nitrogen compounds such as allylamine and allylurea, etc.; and unsaturated organic silicon compounds, such as vinyl trichlorosilane, vinylmethyl dichlorosilane, divinyl dichlorosilane, allyl trichlorosilane, vinyltrimethoxysilane, etc.

The unsaturated reactant can therefor be characterized as an organic compound which may be a hydrocarbon or a hydrocarbon containing sulfur, oxygen, silicon and/or nitrogen hetero atoms having in total about 3 to 20 carbon, or carbon and hetero, atoms in straight, branched or cyclic configuration. These organic compounds may further have various halo substituents, such as fluorine and/or chlorine and/or bromine. It is clear that so long as the reactant in question has an unblocked and unhindered carbon to carbon olefinic or acetylenic unsaturation which is capable of being reacted with a hydrogen silane in a hydrosilylation reaction, such is suited to use in this invention and such hydrosilylation reaction will be profitably catalyzed by the platinum complex compound catalyst hereof.

Suitable hydrogen silanes are trichlorosilane, methyl dichlorosilane, dimethylchlorosilane, ethyldichlorosilane, trimethoxysilane, triethoxysilane and other similar hydrogen silanes which in each silicon atom is substituted with one or two hydrogens and has as the other two or three substituents alkyl, particularly lower alkyl groups containing up to about 6 carbon atoms in the longest straight chain; alkoxy, particularly lower alkoxy containing up to about 6 carbon atoms in the longest straight chain; aryl, particularly monocyclic aryl, containing up to 5 substituents on the ring each of which may be a lower alkyl or lower alkoxy, aryloxy, particularly monocyclic aryloxy containing up to 5 substituents on the ring each of which may be lower alkyl or lower alkoxy; cycloalkyl, particularly monocyclic cycloalkyl having four to twelve, preferably five to seven, carbon atoms in the ring and containing up to one less than the number of ring carbon constitutents of substituents each of which may be lower alkyl or lower alkoxy; cycloalkoxy, particularly monocyclic cycloalkoxy having 4 to 12, preferably 5 to 7, carbon atoms in the ring and containing up to one less than the number of ring carbon constituents of substituents each of which may be lower alkyl or lower alkoxy; or the like substituents containing one or more hetero atoms such as oxygen, sulfur, nitrogen and/or silicon atoms as integral constituents of such substituent groups. In choosing appropriate substituents on the silicon atom of the hydrogen silane, care should be exercized to choose such substituents which are substantially inert to themselves, each other and their environment during the hydrosilylation reaction described herein unless it is desired to particularly induce secondary reactions during the hydrosilylation reaction. Thus for example, under ordinary circumstances it would be undesirable to have an amino, chloro silane, but under special circumstances this might well be particularly desirable.

It is within the scope of this invention to react a single unsaturated reactant with a single hydrogen silane or to react mixtures of one or both reactants as desired. Similarly, it is preferred to use a single platinum-ketone catalyst, however, mxtures of two or more platinum-ketone catalysts according to the definition thereof herein are also considered to be useful and within the purview of this invention.

This invention will be illustrated by the following Examples which are not to be considered as limiting on or determinative of the scope of this invention.

EXAMPLE 1

In a 10-liter flask provided with stirrer, reflux condenser, internal thermometer and two dropping funnels, one filled with 2.85 kg of allyl glycidyl ether and the other with 3.05 kg of trimethoxysilane, 500 ml of allyl glycidyl ether or gamm-glycidyloxypropyltrimethoxysilane was heated to 130° C. Then 1 ml of an 0.01 molar solution of the mesityl oxide-platinum dichloride complex in acetone was added and the reaction was allowed to take place with rapid stirring and the simultaneous feeding in of the two reactants, within about 20 minutes. The internal temperature was kept between 130° C and 140° C by slight external cooling and by regulating the feed. This was followed by vacuum distillation producing 5.4 kg of γ-glycidyloxypropyltrimethoxysilane boiling at $BP_{0.05}$ 81° C ($n_D^{20}$: 1.4290, $d_4^{20}$: 1.073).

EXAMPLE 2 (For comparative purposes)

A comparative experiment analogous to Example 1, using hexachloroplatinic acid in the form of an 0.01 molar solution in isopropanol, showed that the reaction took considerable longer. Combining of the reactants took 2 hours. Stirring continued for 2 hours more, with an input of heat. After that a residual content of 26% of the added amount of trimethoxysilane was determined (by measuring the hydrogen volume separated from 1 ml of substrate with NaOH). Distillation of the product produced γ-glycidyloxypropyltrimethoxysilane in a yield of 66% of the trimethoxysilane feed.

EXAMPLE 3 (For comparative purposes)

Another comparative experiment analogous to Example 1, using dichloroplatinic-bis-acetylacetonate in the form of an 0.01 molar solution in acetone, also resulted in a slower reaction. Combining of the reactants again required 2 hours. After another 2 hours of stirring with an input of heat, a residual content of 22% trimethoxysilane was measured as described in the foregoing example. Vacuum distillation of the reaction product yielded 72% γ-glycidyloxypropyltrimethoxysilane was obtained.

EXAMPLE 4

In a manner analogous to Example 1, 1.42 kg of 2-allyloxymethyltetrahydrofuran (prepared similarly to W.R. Kirner, J. Am. Chem. Soc. 52 (1930) pp. 3251-6 from allyl chloride and tetrahydrofurfuryl alcohol with KOH; B.P. 183–185° C, $n_D^{20}$ 1.4493) was reacted with 1.64 kg of triethoxysilane using 1 ml of an 0.01 molar solution of mesityl oxide-platinum dichloride complex in acetone. The reaction again took place in 20 minutes at 130°–140° C. Distillation of the reaction product yielded 3.36 kg of 3-[tetrahydrofurfuryl-(2)-methyl]-oxypropyltriethoxysilane, B.P.$_{.2}$: 1.27°–129° C ($n_D^{20}$: 1.4330). Elementary analysis compouted to $C_{14}H_{30}O_5Si$ (molecular weight: 306):

|  | C | H | Si |
|---|---|---|---|
| Found: | 54.7% | 9.4% | 9.5% |
| Calculated: | 54.8% | 9.8% | 9.2% |

Molecular weight determination: 300 (lowering of freezing point in benzene method).

EXAMPLE 5

700 g of 2-allyloxymethyltetrahydrofuran were placed in a 10-liter flask and heated to 130° C. 1 ml of catalyst (of the composition given in Example 1) was added. Then the reaction was initiated by starting the trimethoxysilane feed. The reaction started immediately, which was indicated by a strong exothermicity. Within 20 minutes a total of 4026 g of trimethoxysilane and 4000 g of 2-allyloxymethyltetrahydrofuran were added the reaction was allowed to continue at 130°–140° C with moderate external cooling. Distillation of the reaction product yielded 5715 g of 3-tetrahydrofurfuryl-(2)-methyloxypropyltrimethoxysilane, B.P. 121° C at 2 mm mercury column ($n_D^{20}$: 1.4361). Elementary analysis computed to $C_{11}H_{24}O_5Si$:

|  | C | H | Si |
|---|---|---|---|
| Found: | 49.9 | 9.1 | 10.5 |
| Calculated: | 50.0 | 9.1 | 10.6 |

The 2-allyloxymethyltetrahydrofuran had been prepared analogously to W.R. Kirner, J. Am. Chem. Soc. 52 (1930) pp. 3251-6, from allyl chloride and tetrahydrofurfuryl alcohol in the presence of a slight excess of concentrated soda lye. The boiling point is 183°–185° C.

Transesterification of the trimethyl ester with ethanol yielded 3-tetrahydrofurfuryl-(2)-methyloxypropyltriethoxysilane, BP 129° C at 2 mm mercury column ($n_D^{20}$: 1.4330). Elementary analysis computed for $C_{14}H_{30}O_5Si$ (molecular weight 306):

|  | C | H | Si |
|---|---|---|---|
| Found: | 54.7 | 9.4 | 9.5 |
| Calculated: | 54.8 | 9.8 | 9.2 |

Molecular weight determination: 300 (lowering of freezing point in benzene method).

EXAMPLE 6

In a 4-liter flask with stirrer, reflux condenser, internal thermometer and two dropper funnels, one filled with 800 g of allyl acetate and the other with 1.355 kg of trichlorosilane, 200 ml of allyl acetate was heated to 65° C. Then the heat source was removed, 1 ml of an 0.01 molar solution of mesityl oxide-platinum dichloride complex in allyl acetate was added, and the reaction was allowed to complete itself within 8 minutes while stirring was performed and the two reactants were fed in simultaneously. During that period the temperature rose to 105° C due to self-heating. After that no more silane hydrogen was detected analytically. Distillation of the reaction product yielded 2.28 kg of 3-acetyloxypropyltrichlorosilane, BP$_{20}$: 98°–100° C; $n_D^{20}$: 1.4359.

EXAMPLE 7

184 g of 2-ethylcapronic acid allyl ester (prepared from the free acid and allyl alcohol by azeotropic esterification in benzene in the presence of p-toluenesulfonic acid; BP$_{18}$: 95° C; $n_D^{20}$: 1.4298) was heated to 75° C in a three-necked flask provided with stirrer, reflux condenser, internal thermometer and dropping funnel. Then 0.1 ml of an 0.01 molar solution of mesityl oxide-platinum dichloride catalyst complex in acetone was stirred in, and a quantity of 164 g of triethoxysilane was fed in from the dropping funnel within a 6-minute period, during which the temperature rose to 99° C. 10 minutes after the triethoxysilane feed was completed, no more silane hydrogen was analytically detectable. Vacuum distillation of the product yielded 322 g of 3-(2'-ethylcaproyloxy)-propyltriethoxysilane, BP$_1$: 134°–138° C.

EXAMPLE 8

2 moles of trichlorosilane were heated in a common laboratory stirring vessel to 55° C. 0.1 ml of an 0.01 molar solution of mesityl oxide-platinum dichloride complex catalyst in acetone was added, and 2 moles of allyl methacrylate was added drop by drop under nitrogen over a period of 10 minutes with intense stirring. The internal temperature was in the meantime kept below 62° C, by external cooling. After another 8 minutes of stirring at about 60° C, no more silane hydrogen could be detected. Distillation of the product yielded 3-methacryloxypropyltrichlorosilane, (BP$_{0.5}$ = 66° C) in a yield of about 97%, with a residue of about 2%.

EXAMPLE 9

In a flow-through reactor of glass with a double mantle heated to 64° C, an equimolar mixture of trimethoxysilane and allylmethacrylate containing 0.2 ml of the same catalyst solution used in Example 8 for each mole of mixture, was reacted with a residence time of 440 sec. When the reaction product left the reactor no more silane hydrogen can be detected in it. It is of the quality required for technical applications.

What is claimed is:

1. In the process of hydrosilylation with a hydrogen silane of the formula:

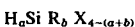

wherein *a* is 1 or 2;

*b* is 0 or 1;

X is alkoxy, cycloalkoxy, aryloxy, or halo; and R is alkoxy cycloalkoxy, aryloxy, halo, alkyl, cycloalkyl or aryl with an organic compound containing carbon to carbon aliphatic unsaturation; the improvement which comprises catalyzing said hydrosilylation reaction with a platinum complex compound of the formula:

wherein *a* is 1 or 2; and $R^1$ is an olefinically unsaturated ketone selected from the group consisting of butenone, phorone, isophorone, dibenzalacetone and mesityl oxide.

2. Process claimed in claim 1 wherein said aliphatic unsaturated compound is selected from the group consisting of ethylene, propylene, 1,1,1-trifluoropropene-2, butene-1, butene-2, isobutene, octene-1, decene-1, cyclohexene, styrene, cyclopentadiene, acetylene, propine, butine-2, divinyl ether, diallyl ether, ethylene glycol diallyl ether, diethylene glycol diallyl ether, polyethylene glycol diallyl ether, polypropylene glycol diallyl ether, glycidyl allyl ether, 2-allyloxymethyl tetrahydrofuran, 2,2-dimethyl-4-allyloxymethyl-dioxolane, 4-allyloxy-dioxolone-2, 2-allyloxy heptafluoro-propane, 2-allyloxy-1,1,1,3,3,3-hexafluoro-propane, vinyl acetate, vinyl propionate, vinyl thioacetate, vinyl 2-ethyl capronate, vinyl laurate, divinyl isophthalate, divinyl dephthalato, vinyl chloride, allyl amine, allyl urea, allyl acetate, allyl propionate, allyl thioacetate, allyl-2-ethyl capronate, allyl laurate, diallyl isophthalate, diallyl terephthalate, allyl chloride, vinyl trichlorosilane, vinyl methyldichlorosilane, divinyl dichlorosilane, allyl trichlorosilane, vinyltri-methoxy silane and allyl methacrylate.

3. Process as claimed in claim 1 wherein said catalyst is present in a proportion of about $10^{-2}$ to $10^{-8}$ millimoles per mole of hydrogen silane reactant.

4. Process as claimed in claim 1 wherein said catalyst is present in a proportion of about $10^{-3}$ to $10^{-6}$ millimoles per mole of hydrogen silane reactant.

5. Process as claimed in claim 1 carried out continuously with a residence time of about 1 to 20 minutes.

6. Process as claimed in claim 1 including maintaining the reaction mixture thereof in admixture for about 2 to 10 minutes after cessation of addition of reactants.

7. Process as claimed in claim 1 carried out at about 130° to 140° C.

8. Process as claimed in claim 1 including dissolving said catalyst in a solvent; and mixing said solution with a small proportion of one of the reactants; and then adding additional reactants thereto.

9. Process as claimed in claim 1 wherein the catalyst is a mesityloxide-platinum dichloride complex.

10. Process according to claim 9 wherein said organic compound containing carbon to carbon aliphatic unsaturation is 2-allyloxymethyltetrahydrofuran.

11. Process according to claim 10 wherein the hydrogen silane is trimethoxy silane.

12. Process according to claim 10 wherein the hydrogen silane is triethoxy silane.

13. Process according to claim 9 wherein the hydrogen silane is trichlorosilane.

14. Process according to claim 13 wherein the organic compound containing carbon to carbon aliphatic unsaturation is allylacetate.

15. Process according to claim 13 wherein the organic compound containing carbon to carbon aliphatic unsaturation is allylmethacrylate.

16. Process according to claim 9 wherein the silane is triethoxy silane.

17. Process according to claim 16 wherein the organic compound containing carbon to carbon aliphatic unsaturation is 2-ethylcapronic acid allyl ester.

18. Process according to claim 9 wherein the silane is trimethoxy silane.

19. Process according to claim 18 wherein the organic compound containing carbon to carbon aliphatic unsaturation is allylmethacrylate.

20. Process according to claim 18 wherein the organic compound containing carbon to carbon aliphatic unsaturation is allylglycidyl ether.

* * * * *

UNITED STATES PATENT OFFICE
CERTIFICATE OF CORRECTION

Patent No. 4,028,384　　　　　　　　　Dated June 7, 1977

Inventor(s) Hans-Joachim Vahlensieck et al.

It is certified that error appears in the above-identified patent and that said Letters Patent are hereby corrected as shown below:

Column 3, line 9, change "dihenzalacetone" to read -- dibenzalacetone --.

Column 3, line 35, change "dephthalato" to read -- dephthalate --.

Signed and Sealed this

Eighth Day of November 1977

[SEAL]

Attest:

RUTH C. MASON　　　　　　LUTRELLE F. PARKER
Attesting Officer　　　　Acting Commissioner of Patents and Trademarks